(12) United States Patent
Grollier et al.

(10) Patent No.: US 7,018,428 B2
(45) Date of Patent: Mar. 28, 2006

(54) PROCESS FOR THE PREPARATION OF A DYEING COMPOSITION FOR THE DYEING OF KERATINOUS FIBERS FROM PRESSURIZED STEAM

(75) Inventors: Jean-François Grollier, Paris (FR); Roland De La Mettrie, Le Vesinet (FR); François Cottard, Levallois-Perret (FR)

(73) Assignee: L'Oreal, Paris (FR)

( * ) Notice: Subject to any disclaimer, the term of this patent is extended or adjusted under 35 U.S.C. 154(b) by 361 days.

(21) Appl. No.: 10/626,640

(22) Filed: Jul. 25, 2003

(65) Prior Publication Data

US 2004/0255400 A1 Dec. 23, 2004

Related U.S. Application Data

(60) Provisional application No. 60/408,898, filed on Sep. 9, 2002.

(30) Foreign Application Priority Data

Jul. 26, 2002 (FR) .................... 02 09515

(51) Int. Cl.
*A61K 7/13* (2006.01)

(52) U.S. Cl. ............... 8/405; 8/406; 8/408; 8/410; 8/411; 8/412; 8/421; 8/426; 132/208; 132/212; 424/401; 424/70.6

(58) Field of Classification Search ............. 8/405, 8/406, 408, 410, 411, 412, 426; 132/208, 132/212; 424/401
See application file for complete search history.

(56) References Cited

U.S. PATENT DOCUMENTS

| | | | | |
|---|---|---|---|---|
| 2,688,911 A | 9/1954 | Hochmayr | ............ | 99/305 |
| 4,003,699 A | 1/1977 | Rose et al. | ............ | 8/10.2 |
| 4,486,762 A | 12/1984 | Okamoto et al. | ........... | 346/207 |
| 5,061,289 A | 10/1991 | Clausen et al. | ........... | 8/405 |
| 5,380,340 A | 1/1995 | Neunhoeffer et al. | ......... | 8/409 |
| 5,496,377 A * | 3/1996 | Samain et al. | ........... | 8/414 |
| 5,520,706 A | 5/1996 | Samain et al. | ........... | 8/406 |
| 5,708,151 A | 1/1998 | Möckli | ............ | 534/608 |
| 5,725,603 A | 3/1998 | Audousset et al. | ........... | 8/405 |
| 5,766,576 A | 6/1998 | Löwe et al. | ............ | 424/62 |
| 5,897,899 A | 4/1999 | Fond | ............ | 426/112 |
| 6,099,592 A | 8/2000 | Vidal et al. | ............ | 8/409 |

FOREIGN PATENT DOCUMENTS

| | | |
|---|---|---|
| DE | 23 59 399 | 6/1975 |
| DE | 32 43 870 | 6/1983 |
| DE | 38 43 892 | 6/1990 |
| DE | 41 33 957 | 4/1993 |
| DE | 195 43 988 | 5/1997 |
| EP | 0 384 796 | 8/1990 |
| EP | 0 512 470 | 11/1992 |
| EP | 0 659 396 | 6/1995 |
| EP | 0 659 397 | 6/1995 |
| EP | 0 659 399 | 6/1995 |
| EP | 0 714 954 | 6/1996 |
| EP | 0 770 375 | 5/1997 |
| FR | 2 733 749 | 11/1996 |
| FR | 2 801 308 | 5/2001 |
| GB | 1 026 978 | 4/1966 |
| GB | 1 153 196 | 5/1969 |
| GB | 1 512 823 | 6/1978 |
| JP | 2-19576 | 1/1990 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/16765 | 5/1996 |
| WO | WO 99/03753 | 1/1999 |
| WO | WO 00/56629 | 9/2000 |

OTHER PUBLICATIONS

English language Derwent Abstract of EP 0 384 796, Aug. 29, 1990.
English language Derwent Abstarct of EP 0 770 375, May 2, 1997.
English language Derwent Abstract of FR 2 801 308, May 25, 2001.
English language Derwent Abstract of JP 2-19576, Jan. 23, 1990.

* cited by examiner

*Primary Examiner*—Eisha Elhilo
(74) *Attorney, Agent, or Firm*—Finnegan Henderson Farabow Garrett & Dunner, L.L.P.

(57) ABSTRACT

Disclosed herein is a process for the preparation of a dyeing composition intended for dyeing keratinous fibers comprising percolating pressurized steam through a suitable pulverulent compound, as well as a device for packaging such a compound and a dyeing process using such a dyeing composition.

22 Claims, No Drawings

PROCESS FOR THE PREPARATION OF A DYEING COMPOSITION FOR THE DYEING OF KERATINOUS FIBERS FROM PRESSURIZED STEAM

This application claims benefit of U.S. Provisional Application No. 60/408,898, filed Sep. 9, 2002.

Disclosed herein is a process for the preparation of a dyeing composition intended for the dyeing of keratinous fibers, for example, human keratinous fibers, such as hair, and a process for dyeing keratinous fibers using this composition.

It is known to dye keratinous fibers such as human hair with dyeing compositions comprising oxidation dye precursors, generally known as oxidation bases, such as ortho- and para-phenylenediamines, ortho- and para-aminophenols, and heterocyclic compounds. These oxidation bases are colorless or weakly colored compounds which, in combination with oxidizing substances, can give rise to colored compounds by an oxidative coupling process.

It is also known that the shades obtained with these oxidation bases can be varied by combining them with couplers or coloring modifiers. The couplers or coloring modifiers can be chosen, for example, from aromatic meta-diamines, meta-aminophenols, meta-diphenols and certain heterocyclic compounds, such as indole compounds.

The variety of the molecules employed as oxidation bases and couplers can make it possible to obtain a rich palette of colors.

It is also known to dye keratinous fibers by direct dyeing. The process conventionally used in direct dyeing comprises applying direct dyes to keratinous fibers, wherein the direct dyes are colored and the coloring molecules have an affinity for the keratinous fibers, and leaving the dyes to stand and then optionally rinsing the keratinous fibers. The direct dyes can, for example, be chosen from nitrobenzene dyes, anthraquinone dyes, nitropyridine dyes, azo dyes, xanthene dyes, acridine dyes, azine dyes, and methine dyes. These direct dyes can be nonionic, anionic or cationic in nature.

The resulting colorations can be particularly chromatic colorations which, however, may be temporary or semi-permanent because the nature of the interactions that bind the direct dyes to the keratinous fibers and their desorption from the surface and/or from the core of the keratinous fibers are responsible for their low dyeing power and for their poor resistance to being washed or to perspiration.

Dyeing compositions are generally aqueous compositions in which the bases, couplers or direct dyes need to be dissolved. The lack of solubility of these compounds in the dyeing composition can reduce the coloring power of these compositions. Furthermore, this criterion of solubility reduces the number of bases, couplers or direct dyes which can be used for dyeing keratinous fibers.

Furthermore, when these bases, couplers or direct dyes are obtained from natural plant or animal extracts, the extraction of these compounds can prove to be difficult with a low extraction yield.

Processes for dyeing keratinous fibers using steam are already known. These processes comprise applying, in a first step, a conventional dyeing composition to the hair and applying, to the hair coated with this composition, steam for a very short time. These processes can make it possible to improve, for example, the uniformity of the coloration from the roots to the tips.

Disclosed herein is a novel process for preparing a dyeing composition, which can be carried out easily and can make it possible to use a large variety of bases, couplers, and direct dyes, such as those bases, couplers, and direct dyes which are low in solubility.

As disclosed herein, the novel process for preparing a dyeing composition for dyeing keratinous fibers comprises percolating steam under a pressure of at least 3 bar through at least one pulverulent compound capable of generating a solution capable of dyeing keratinous fibers.

By means of this novel process, it is thus possible to use a greater variety of bases, couplers, and direct dyes and thus to obtain a broader range of shades for the coloring of keratinous fibers. Furthermore, this process can make it possible to increase the coloring power of dyeing compositions by better dissolution of the dyes or dye precursors in the dyeing medium and better diffusion in the medium to be dyed.

Further disclosed herein is a packaging device, which can make it possible to use the preparation process disclosed herein.

Even further disclosed herein is a dyeing process using the dyeing composition obtained by the preparation process disclosed herein.

The preparation process disclosed herein can be carried out in a conventional device, which can make it possible to generate pressurized steam. Such a device comprises a pressure-resistant chamber equipped with a heating unit and a circuit for conveying the steam produced to the compound capable of generating a solution capable of dyeing keratinous fibers. According to another embodiment, the device additionally comprises a water tank and a pump, which can make it possible to convey water to the chamber.

A useful device for implementing the preparation process disclosed herein is, for example, a coffee machine of the "espresso" type. Such machines are well known in the art. For example, these machines are disclosed in Patents AT 168 405, U.S. Pat. No. 2,688,911, DE 3243870, and IT 1 265 636.

The steam thus produced can percolate through the pulverulent compound or compounds capable of generating a solution capable of dyeing keratinous fibers. A fluid dyeing composition can thus be obtained, which can be applied directly to keratinous fibers or can be mixed with a medium appropriate for dyeing keratinous fibres or with any conventional dyeing composition known in the art.

In one embodiment, the percolation is carried out with steam under a pressure of at least 4 bar, such as at least 10 bar and further such as from 10 to 30 bar.

The compounds capable of generating a solution capable of dyeing keratinous fibers can be used in the form of a powder placed directly in the device, which generates pressurized steam in a receptacle intended for this use. They can be packaged in a specific packaging device comprising a closed housing delimited by at least one wall at least partially permeable to steam under a pressure of at least 3 bar. Such devices are disclosed, for example, in Patent Applications WO 00/56629, EP 512 470, and WO 99/03753.

In one embodiment, the housing is delimited by two sealed sheets. In another embodiment, the housing is delimited by a container closed by a lid.

These devices can be manufactured from woven or non-woven materials made of plastic, of plant material, such as cellulose, of metal, such as aluminium, or of composite. Such devices are disclosed, for example, in Patent Applications WO 00/56629, EP 512 470, and WO 99/03753.

The pulverulent compounds capable of generating a solution capable of dyeing keratinous fibers are well known in the art. Such compounds are chosen, for example, from oxidation bases, couplers, and direct dyes. These compounds can be compounds synthesized conventionally or extracted from plant or animal species. The extract can be obtained from the entire organism or from part of the organism, for example, the leaves and the roots. Active substances, which can be extracted from plant species are, for example, hydroxylated quinone, indigoids, hydroxyflavones, santalin A and santalin B, isatin and its derivatives, and brasilin and its hydroxylated derivative. The plant species, which may be used herein are, for example, henna, indigo, mayweed, annatto, and alkanet. Animal species, which can be used are, for example, cochineal insects.

The oxidation bases are generally chosen from para-phenylenediamines, bisphenylalkylenediamines, para-aminophenols, ortho-aminophenols, heterocyclic bases and the addition salts thereof.

Mention may be made, among the para-phenylenediamines, by way of example, of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, N,N-diethyl-3-methyl para-phenylenediamine, N,N-bis(β-hydroxyethyl)-para-phenylenediamine, N,N-bis(β-hydroxyethyl)amino-2-methyl para-phenylenediamine, N,N-bis(β-hydroxyethyl) amino-2-chloro para-phenylenediamine, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-(ethyl)-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 4-aminophenylpyrrolidine, 2-thienyl-para-phenylenediamine, 2-(β-hydroxyethylamino)-5-aminotoluene, 3-hydroxy-1-(4'-aminophenyl)pyrrolidine and the acid addition salts thereof.

Among the para-phenylenediamines mentioned above, para-phenylenediamine, para-toluylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine and the acid addition salts can, for example, be used.

Mention may be made, among the bisphenylalkylenediamines, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis(4-amino-phenyl)tetramethylenediamine, N,N'-bis(4-methylaminophenyl)tetramethylenediamine, N,N'-bis (ethyl)-N,N'-bis(4'-amino-3'-methylphenyl) ethylenediamine, 1,8-bis(2,5-diaminophenoxy)-3,6-dioxaoctane and the acid addition salts thereof.

Mention may be made, among the para-aminophenols, by way of example, of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-(β-hydroxyethyl)aminomethyl)phenol, 4-amino-2-fluorophenol and the acid addition salts thereof.

Mention may be made, among the ortho-aminophenols, by way of example, of 2-aminophenol, 2-amino-5-methylphenol, 2-amino-6-methylphenol, 5-acetamido-2-aminophenol and the acid addition salts thereof.

Mention may be made, among the heterocyclic bases, by way of example, of pyridine derivatives, pyrimidine derivatives, and pyrazole derivatives.

Mention may be made, among the pyridine derivatives, of the compounds disclosed, for example, in Patents GB 1 026 978 and GB 1 153 196, such as 2,5-diaminopyridine; 2-[(4-methoxyphenyl)amino]-3-aminopyridine; 2,3-diamino-6-methoxypyridine; 2-[(β-methoxyethyl)amino]-3-amino-6-methoxypyridine; 3,4-diaminopyridine; and the acid addition salts thereof.

Other pyridine oxidation bases, which can be used herein, are, for example, the 3-aminopyrazolo[1,5-a]pyridine oxidation bases and the addition salts thereof disclosed, for example, in Patent Application FR 2 801 308. Mention may be made, by way of example, of pyrazolo[1,5-a]pyridin-3-ylamine; 2-(acetylamino)pyrazolo[1,5-a]pyridin-3-ylamine; 2-(morpholin-4-yl)pyrazolo[1,5-a]pyridin-3-ylamine; 3-aminopyrazolo[1,5-a]pyridine-2-carboxylic acid; 2-methoxypyrazolo[1,5-a]pyridin-3-ylamine; (3-aminopyrazolo[1,5-a]pyridin-7-yl)methanol; 2-(3-aminopyrazolo[1,5-a]pyridin-5-yl)ethanol; 2-(3-aminopyrazolo[1,5-a]pyridin-7-yl) ethanol; (3-aminopyrazolo[1,5-a]pyridin-2-yl)methanol; 3,6-diaminopyrazolo[1,5-a]pyridine; 3,4-diaminopyrazolo [1,5-a]pyridine; pyrazolo[1,5-a]pyridine-3,7-diamine; 7-(morpholin-4-yl)pyrazolo[1,5-a]pyridin-3-ylamine; pyrazolo[1,5-a]pyridine-3,5-diamine; 5-(morpholin-4-yl)pyrazolo[1,5-a]pyridin-3-ylamine; 2-[(3-aminopyrazolo[1,5-a]pyridin-5-yl) (2-hydroxyethyl)amino]ethanol; 2-[(3-aminopyrazolo[1,5-a]pyridin-7-yl) (2-hydroxyethyl)amino] ethanol; 3-aminopyrazolo[1,5-a]pyridin-5-ol; 3-aminopyrazolo[1,5-a]pyridin-4-ol; 3-aminopyrazolo[1,5-a]pyridin-6-ol; 3-aminopyrazolo[1,5-a]pyridin-7-ol; and the addition salts thereof.

Mention may be made, among the pyrimidine derivatives, of the compounds disclosed, for example, in Patents DE 2 359 399, JP 88-169571, JP 05-63124, EP 0 770 375 and Patent Application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives, such as those mentioned in Patent Application FR-A-2 750 048 and among which may be mentioned pyrazolo[1,5-a]pyrimidine-3,7-diamine; 2,5-dimethylpyrazolo[1,5-a]pyrimidine-3,7-diamine; pyrazolo [1,5-a]pyrimidine-3,5-diamine; 2,7-dimethylpyrazolo[1,5-a]pyrimidine-3,5-diamine; 3-aminopyrazolo[1,5-a] pyrimidin-7-ol; 3-aminopyrazolo[1,5-a]pyrimidine-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimid in-7-yl) (2-hydroxyethyl)amino]ethanol, 2-[(7-aminopyrazolo[1,5-a]pyrimid in-3-yl) (2-hydroxyethyl)amino]ethanol, 5,6-dimethylpyrazolo[1,5-a]pyrimidine-3,7-diamine, 2,6-dimethylpyrazolo [1,5-a]pyrimidine-3,7-diamine, 2,5,N7,N7-tetramethylpyrazolo[1,5-a]pyrimidine-3,7-diamine, 3-amino-5-methyl-7-(imidazolylpropylamino)pyrazolo[1,5-a]pyrimidine and the acid addition salts thereof and their tautomeric forms, when a tautomeric equilibrium exists.

Mention may be made, among the pyrazole derivatives, of the compounds disclosed in Patents DE 3 843 892 and DE 4 133 957 and Patent Applications WO 94/08969, WO 94/08970, FR-A-2 733 749 and DE 195 43 988, such as 4,5-diamino-1-methylpyrazole, 4,5-diamino-1-(β-hydroxyl) pyrazole, 3,4-diaminopyrazole, 4,5-diamino-1-(4'-chlorobenzyl)pyrazole, 4,5-diamino-1,3-dimethylpyrazole, 4,5-diamino-3-methyl- 1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-(tert-butyl)-1-methylpyrazole, 4,5-diamino-1-(tert-butyl)-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1-methylpyrazole and the acid addition salts thereof.

The couplers which can be used herein are, for example, chosen from meta-phenylenediamine, meta-aminophenol, meta-diphenol, naphthalene and heterocyclic couplers and the addition salts thereof.

Mention may be made, by way of example, of 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylened ioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)-toluene and the acid addition salts thereof.

Generally, the addition salts of the oxidation bases and couplers which can be used herein are chosen, for example, from the acid addition salts, such as hydrochlorides, hydrobromides, sulphates, citrates, succinates, tartrates, lactates, tosylates, benzenesulphonates, phosphates, and acetates, and the base addition salts, such as sodium hydroxide, potassium hydroxide, ammonia, amines, and alkanolamines.

The direct dyes which can be used herein are chosen, for example, from nitrobenzene direct dyes, azo direct dyes, quinone direct dyes such as anthraquinone direct dyes, azine direct dyes, triarylmethane direct dyes, indoamine direct dyes, natural direct dyes, and methine direct dyes, wherein the direct dyes may be non-ionic, anionic, or cationic.

Mention may be made, among the nitrobenzene direct dyes which can be used herein, for example, of the following compounds:

1,4-diamino-2-nitrobenzene,
1-amino-2-nitro-4-(β-hydroxyethylamino)benzene,
1-amino-2-nitro-4-(bis(β-hydroxyethyl)amino)benzene,
1,4-bis(β-hydroxyethylamino)-2-nitrobenzene,
1-(β-hydroxyethylamino)-2-nitro-4-(bis(β-hydroxyethyl)amino)benzene,
1-(β-hydroxyethylamino)-2-nitro-4-aminobenzene,
1-(β-hydroxyethylamino)-2-nitro-4-((ethyl) (β-hydroxyethyl)amino)benzene,
1-amino-3-methyl-4-(β-hydroxyethylamino)-6-nitrobenzene,
1-amino-2-nitro-4-(β-hydroxyethylamino)-5-chlorobenzene,
1,2-diamino-4-nitrobenzene,
1-amino-2-(β-hydroxyethylamino)-5-nitrobenzene,
1,2-bis(β-hydroxyethylamino)-4-nitrobenzene,
1-amino-2-(tris(hydroxymethyl)methylamino)-5-nitrobenzene,
1-hydroxy-2-amino-5-nitrobenzene,
1-hydroxy-2-amino-4-nitrobenzene,
1-hydroxy-3-nitro-4-aminobenzene,
1-hydroxy-2-amino-4,6-dinitrobenzene,
1-(β-hydroxyethyloxy)-2-(β-hydroxyethylamino)-5-nitrobenzene,
1-methoxy-2-(β-hydroxyethylamino)-5-nitrobenzene,
1-(β-hydroxyethyloxy)-3-methylamino-4-nitrobenzene,
1-(β,γ-dihydroxypropyloxy)-3-methylamino-4-nitrobenzene,
1-(β-hydroxyethylamino)-4-(β,γ-dihydroxypropyloxy)-2-nitrobenzene,
1-(β,γ-dihydroxypropylamino)-4-trifluoromethyl-2-nitrobenzene,
1-(β-hydroxyethylamino)-4-trifluoromethyl-2-nitrobenzene,
1-(β-hydroxyethylamino)-3-methyl-2-nitrobenzene,
1-(β-aminoethylamino)-5-methoxy-2-nitrobenzene,
1-hydroxy-2-chloro-6-ethylamino-4-nitrobenzene,
1-hydroxy-2-chloro-6-amino-4-nitrobenzene,
1-hydroxy-6-(bis(β-hydroxyethyl)amino)-3-nitrobenzene,
1-(β-hydroxyethylamino)-2-nitrobenzene, and
1-hydroxy-4-(β-hydroxyethylamino)-3-nitrobenzene.

Mention may be made, among the azo direct dyes, of the cationic azo dyes disclosed in Patent Applications WO 95/15144, WO 95/01772, and EP 714 954.

Mention may, for example, be made, among these compounds, of the following dyes:
1,3-dimethyl-2-[[4-(dimethylamino)phenyl]azo]-1H-imidazolium chloride, 1,3-dimethyl-2-[(4-aminophenyl)azo]-1H-imidazolium chloride, and 1-methyl-4-[(methylphenylhydrazono)methyl]pyridinium methyl sulphate.

Mention may also be made, among the azo direct dyes, of the following dyes, described in the Color Index International, $3^{rd}$ edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, and Disperse Black 9

Mention may also be made of 1-(4'-aminodiphenylazo)-2-methyl-4-(bis(β-hydroxyethyl)amino)benzene and 4-hydroxy-3-(2-methoxyphenylazo)-1-naphthalenesulphonic acid.

Mention may be made, among the quinone direct dyes, of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, and Basic Blue 99, and the following compounds: 1-N-methylmorpholiniumpropylamino-4-hydroxyanthraquinone, 1-aminopropylamino-4-(methylamino)anthraquinone, 1-(aminopropylamino)anthraquinone, 5-(β-hydroxyethyl)-1,4-diaminoanthraquinone, 2-(aminoethylamino)anthraquinone, and 1,4-bis(β,γ-dihydroxypropylamino)anthraquinone.

Mention may be made, among the azine dyes, of the following dyes: Basic Blue 17 and Basic Red 2.

Mention may be made, among the triarylmethane dyes, which can be used herein, of the following dyes: Basic Green 1, Acid Blue 9, Basic Violet 3, Basic Violet 14, Basic Blue 7, Acid Violet 49, Basic Blue 26, and Acid Blue 7.

Mention may be made, among the indoamine dyes which can be used herein, of the following compounds:
2-(β-hydroxyethylamino)-5-[4'-(bis(β-hydroxyethyl)amino) anilino]-1,4-benzoquinone,
2-(β-hydroxyethylamino)-5-(2'-methoxy-4'-aminoanilino)-1,4-benzoquinone,
3-[N-(2'-chloro-4'-hydroxyphenyl)acetylamino]-6-methoxy-1,4-benzoquinone imine,
3-[N-[3'-chloro-4'-(methylamino)phenyl]ureido]-6-methyl-1,4-benzoquinone imine, and
3-[[4'-[N-(ethyl, carbamylmethyl)amino]phenyl]ureido]-6-methyl-1,4-benzoquinone imine.

Mention may be made, among the natural direct dyes which can be used herein, of lawsone, juglone, alizarin, purpurin, carminic acid, kermesic acid, purpurogallin, protocatechualdehyde, indigo, isatin, curcumin, spinulosin, and apigenidin. Use may also be made of extracts or decoctions comprising these natural dyes such as, for example, cataplasms or henna-based extracts.

In the process disclosed herein, the compound capable of generating a solution capable of dyeing keratinous fibers can be chosen from at least one of oxidation bases, couplers, and direct dyes.

The compound or compounds, which can be used in the process disclosed herein, can be employed as a mixture with a support, such as a pulverulent support. Such a support can be made of organic, inorganic or plant material acting as pulverulent fillers and adjuvants, which can facilitate the processing and/or the dyeing. The inorganic fillers can be chosen from clays and salts. The organic fillers can be polymers, such as sugars (mono-, oligo- or polysaccharides). The plant fillers can be powders chosen from powders derived from roots, leaves, and plant proteins. The pulverulent adjuvants can be chosen, for example, from basifying and acidifying agents, such as lysine and citric acid, surfactants, such as lauryl sulphate, reducing agents, such as ascorbic acid and sulphites, and natural and synthetic thickeners.

The preparation process disclosed herein can result in a dyeing composition, which can be used either directly or after addition of various components.

The amount of oxidation bases present in the dyeing composition obtained by the process disclosed herein ranges, for example, from 0.001 to 10% by weight, relative to the total weight of the dyeing composition, further, for example, from 0.005 to 6% by weight, relative to the total weight of the dyeing composition.

The amount of couplers present in the dyeing composition obtained by the process disclosed herein ranges, for example, from 0.001 to 10% by weight, relative to the total weight of the dyeing composition, further, for example, from 0.005 to 6%, by weight, relative to the total weight of the dyeing composition.

The amount of direct dyes present in the dyeing composition obtained by the process disclosed herein ranges, for example, from 0.001 to 20% by weight, relative to the total weight of the dyeing composition, further, for example, from 0.005 to 10% by weight, relative to the total weight of the dyeing composition.

When the dyeing composition obtained by the process disclosed herein is mixed with a medium appropriate for dyeing, such a medium comprises water or a mixture of water and at least one organic solvent in order to dissolve the compounds which would not be sufficiently soluble in water. The at least one organic solvent may be chosen, for example, from lower $C_1$–$C_4$ alkanols, such as ethanol and isopropanol; polyols and polyol ethers, such as 2-butoxyethanol, propylene glycol, propylene glycol monomethyl ether, diethylene glycol monoethyl ether, and diethylene glycol monomethyl ether; and aromatic alcohols, such as benzyl alcohol and phenoxyethanol.

The at least one organic solvent is, for example, present in a proportion ranging from 1 to 40% by weight, relative to the total weight of the dyeing composition and further, for example, from 5 to 30% by weight, relative to the total weight of the dyeing composition.

The dyeing composition can also comprise at least one adjuvant chosen from various adjuvants conventionally used in compositions for dyeing the hair, such as anionic, cationic, nonionic, amphoteric, and zwitterionic surfactants, and the mixtures thereof, anionic, cationic, nonionic, amphoteric, and zwitterionic polymers and the mixtures thereof, inorganic and organic thickening agents such as anionic, cationic, nonionic, and amphoteric polymeric associative thickeners, antioxidants, penetration agents, sequestering agents, fragrances, buffers, dispersing agents, conditioning agents, such as volatile and non-volatile, modified and unmodified silicones, film-forming agents, ceramides, preservatives, and opacifying agents.

The at least one adjuvant is, for example, present in an amount ranging from 0.01 to 20% by weight, relative to the total weight of the dyeing composition.

Of course, a person skilled in the art will take care to choose this or these optional additional compound(s) so that the advantageous properties intrinsically attached to the dyeing composition disclosed herein are not, or not substantially, detrimentally affected by the envisaged addition(s).

The pH of the dyeing composition ranges, for example, from 3 to 12, such as from 5 to 11. The pH can be adjusted to the desired value by using at least one agent chosen from acidifying and basifying agents commonly used in dyeing keratinous fibers or using a conventional buffer system.

Mention may be made, among the acidifying agents, by way of example, of inorganic and organic acids, such as hydrochloric acid, orthophosphoric acid, sulphuric acid, carboxylic acids, such as acetic acid, tartaric acid, citric acid, and lactic acid, and sulphonic acids.

Mention may be made, among the basifying agents, by way of example, of ammonia, alkaline carbonates, alkanolamines, such as mono-, di- and triethanolamines, and the derivatives thereof, sodium hydroxide, potassium hydroxide, and the compounds of following formula (II):

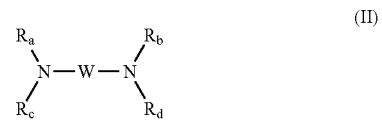

(II)

wherein W is a propylene residue optionally substituted by at least one entity chosen from a hydroxyl group and $C_1$–$C_4$ alkyl radicals; and $R_a$, $R_b$, $R_c$ and $R_d$, which may be identical or different, are each chosen from a hydrogen atom, $C_1$–$C_4$ alkyl radicals, and $C_1$–$C_4$ hydroxyalkyl radicals.

The final dyeing composition can be provided in various forms, such as in the form of liquids, creams, or gels or in any other form appropriate for carrying out dyeing of keratinous fibers such as human hair.

When the compound capable of generating a solution capable of dyeing keratinous fibers comprises at least one oxidation base, the color is then developed using at least one oxidizing agent. According to one embodiment, the dyeing composition is mixed, such as at the time of use, with an oxidizing composition comprising, in a medium appropriate for dyeing, at least one oxidizing agent, wherein the at least one oxidizing agent is present in an amount sufficient to develop a coloration. The mixture obtained is subsequently applied to keratinous fibres. After a leave-in time ranging from 3 to 50 minutes, such as from 5 to 30 minutes, the keratinous fibers are rinsed, washed with a shampoo, rinsed again and then dried.

The at least one oxidizing agent is chosen from oxidizing agents conventionally used for the oxidation dyeing of keratinous fibers chosen, for example, from hydrogen peroxide, urea hydrogen peroxide, alkali metal bromates, persalts, such as perborates and persulphates, peracids and oxidase enzymes, among which may be mentioned peroxidases, 2-electron oxidoreductases, such as uricases, and 4-electron oxygenases, such as laccases. In one embodiment, hydrogen peroxide is used.

The oxidizing composition can further comprise at least one adjuvant chosen from various adjuvants conventionally used in compositions for dyeing the hair and as defined above.

The color can be developed at acidic, neutral or alkaline pH.

The ready-for-use composition, which is finally applied to the keratinous fibers, comprising the dyeing composition and the oxidizing composition, can be provided in various forms, such as in the form of liquids, creams or gels or in any other form appropriate for carrying out dyeing of keratinous fibers such as human hair.

In one embodiment, a henna powder is placed in a commercially available Magimix Nespresso® espresso machine in the receptacle intended to receive a pulverulent compound. The steam produced by the machine is subsequently passed through the pulverulent compound. A dyeing composition is thus obtained, which is ready to be applied to the keratinous fibers.

In another embodiment, a pulverulent composition comprising 4-amino-2-methylphenol and 1-methyl-2-hydroxy-4-aminobenzene as an equimolar mixture is placed in the receptacle of the same espresso machine intended to receive a pulverulent material. Steam produced by the machine is passed through this pulverulent mixture. The dyeing composition thus obtained is brought into contact with an oxidizing agent, such as hydrogen peroxide, before application to the keratinous fibers.

What is claimed is:

1. A process for preparing a dyeing composition for dyeing keratinous fibers, comprising percolating steam under a pressure of at least 3 bar through at least one pulverulent compound capable of generating a solution capable of dyeing keratinous fibers.

2. The process according to claim 1, wherein the keratinous fibers are human keratinous fibers.

3. The process according to claim 2, wherein the human keratinous fibers are hair.

4. The process according to claim 1, wherein the at least one pulverulent compound capable of generating a solution capable of dyeing keratinous fibers is chosen from oxidation bases, couplers, and direct dyes.

5. The process according to claim 4, wherein said oxidation bases are chosen from para-phenylenediamines, bisphenylalkylenediamines, para-aminophenols, ortho-aminophenols, heterocyclic bases, and the addition salts thereof.

6. The process according to claim 4, wherein said couplers are chosen from meta-phenylenediamines, meta-aminophenols, meta-diphenols, naphthalene couplers, heterocyclic couplers, and the addition salts thereof.

7. The process according to claim 4, wherein said direct dyes are chosen from nitrobenzene direct dyes, azo direct dyes, quinone direct dyes, azine direct dyes, triarylmethane direct dyes, indoamine direct dyes, natural direct dyes, and methine direct dyes, wherein said direct dyes may be nonionic, anionic, or cationic.

8. The process according to claim 1, wherein the at least one pulverulent compound capable of generating a solution capable of dyeing keratinous fibers is chosen from compounds obtained from plant or animal species.

9. The process according to claim 8, wherein the compounds obtained from plant species are chosen from hydroxylated quinone, indigoids, hydroxyflavones, santalin A and santalin B, isatin and the derivatives thereof, and brasilin and the hydroxylated derivative thereof.

10. The process according to claim 8, wherein the plant species are chosen from henna, indigo, mayweed, annatto, and alkanet.

11. The process according to claim 8, wherein the animal species are chosen from cochineal insects.

12. The process according to claim 1, wherein the percolation is carried out with steam under a pressure of at least 4 bar.

13. The process according to claim 12, wherein the percolation is carried out with steam under a pressure of at least 10 bar.

14. The process according to claim 13, wherein the percolation is carried out with steam under a pressure ranging from 10 to 30 bar.

15. A process for dyeing keratinous fibers, comprising
preparing a dyeing composition, comprising percolating steam under a pressure of at least 3 bar through at least one pulverulent compound capable of generating a solution capable of dyeing keratinous fibers; and
applying the dyeing composition to the keratinous fibers for a time sufficient to develop a desired coloration.

16. The process according to claim 15, wherein the keratinous fibers are human keratinous fibers.

17. The process according to claim 16, wherein the human keratinous fibers are hair.

18. The process according to claim 15, wherein the at least one pulverulent compound capable of generating a solution capable of dyeing keratinous fibers is chosen from oxidation bases, couplers, and direct dyes.

19. The process according to claim 15, wherein the at least one pulverulent compound capable of generating a solution capable of dyeing keratinous fibers is chosen from compounds obtained from plant and animal species.

20. A device for packaging at least one pulverulent compound capable of generating a solution capable of dyeing keratinous fibers, comprising a closed housing delimited by at least one wall at least partially permeable to steam under a pressure of at least 3 bar, wherein the closed housing comprises the at least one pulverulent compound capable of generating a solution capable of dyeing keratinous fibers.

21. The device according to claim 20, wherein the closed housing is delimited by two sealed sheets.

22. The device according to claim 20, wherein the closed housing is delimited by a container closed by a lid.

* * * * *